United States Patent [19]

Bellet et al.

[11] 4,161,397

[45] Jul. 17, 1979

[54] LIQUID COMBINATION SEED TREATMENT COMPOSITIONS

[75] Inventors: Eugene M. Bellet, Stilwell, Kans.; Madan M. Joshi, Quincy, Ill.

[73] Assignee: Kalo Laboratories, Inc., Kansas City, Mo.

[21] Appl. No.: 822,792

[22] Filed: Aug. 8, 1977

[51] Int. Cl.$^2$ ............................................. C05F 11/08
[52] U.S. Cl. ............................................. 71/7; 71/6; 435/260
[58] Field of Search ................ 71/6, 7, 64 C; 195/59, 195/96; 924/93; 47/DIG. 9, 58

[56] References Cited

U.S. PATENT DOCUMENTS

| | | | |
|---|---|---|---|
| 1,292,332 | 1/1918 | Earp-Thomas | 71/7 |
| 2,376,333 | 5/1945 | Ark | 195/73 |
| 2,911,295 | 11/1959 | Peter | 71/6 |
| 3,034,968 | 5/1962 | Johnston | 195/98 |
| 3,075,887 | 1/1963 | Siliker | 195/101 |
| 3,099,601 | 7/1963 | Davis et al. | 195/96 |
| 3,168,796 | 2/1965 | Scott et al. | 71/7 |
| 3,205,060 | 9/1965 | Lindert | 71/7 |
| 3,616,236 | 10/1971 | Delin | 195/96 |
| 3,898,132 | 8/1975 | Hettrick | 71/6 |
| 3,982,920 | 9/1976 | Cross et al. | 71/64 C |

OTHER PUBLICATIONS

Raun et al., "Encapsulation as a Technique for Formulating Microbial and Chemical Insecticides", J. Eco n. Entomology, S9, No. 3, pp. 620-622.

*Primary Examiner*—Joseph Scovronek
*Assistant Examiner*—Chris P. Konkol
*Attorney, Agent, or Firm*—Watson, Leavenworth, Kelton & Taggart

[57] ABSTRACT

A liquid seed treatment composition is described in which microdried bacteria are flowably suspended in a nonphytotoxic liquid carrier with a chemical substance normally toxic to the bacteria. The bacteria in the compositions exhibit prolonged viability relative to dry, non-fluid formulations. To sustain bacterial viability and effectiveness of the compositions, the compositions are maintained as a liquid colloid in which the ingredients are thoroughly dispersed.

15 Claims, No Drawings

LIQUID COMBINATION SEED TREATMENT COMPOSITIONS

BACKGROUND OF THE INVENTION

Seed treatment compositions historically have provided bacterial inoculation, chemical protection or, in certain instances, supplied micronutrients. These products have often been dry powders employing various dried carriers which are added to the seed before or at planting, although liquid slurries have also been used to pre-treat or preinoculate seed.

Combination products combining both agricultural chemicals and bacteria in the same package as dried powders have also been employed to pre-treat or pre-inoculate seeds. These prior art formulations containing bacteria and chemicals, however, have sometimes exhibited reduced bacterial activity after a period of time. Thus, such formulations have in some instances been found to be virtually without bacterial activity despite the presence of adequate bacteria in the formulations when initially composed.

The lack of uniform effectiveness of prior art formulations in which bacteria have been combined with fungicides and the like can apparently be attributed to the toxic effects of such chemicals on bacteria. Thus during storage, the bacteria are destroyed by the chemicals causing the reduced activity. After a sufficiently long storage period so few bacteria remain viable that the product is substantially without bacterial activity.

To be satisfactory and acceptable, the effectiveness of a seed treating composition must be known with certainty for a reasonable period of time. A seed pretreatment or inoculate composition which is to serve multiple functions must, therefore, provide a means for avoiding the toxic effect of agricultural chemicals on bacteria.

It is therefore the principle object of this invention to provide seed treatment compositions which contain combinations of bacteria and toxic chemicals substances which have a more stable, predictable effectiveness for an increased period of time.

It is an additional object of the invention to provide a means for prolonging the viability and functional activity of bacteria in seed treatment products even in the presence of chemical substances which are normally toxic or deleterious to bacteria.

It is yet another object of the invention to improve seed treating compositions by prolonging bacterial viability, thereby insuring greater populations over time.

It is a further object of the invention to provide a practical means of combining needed toxicants with bacteria in pre-mixed and pre-measured dosages.

These and other objects and advantages of the present invention will be readily apparent to persons skilled in the art from the following description and examples.

SUMMARY OF THE INVENTION

This invention relates to liquid seed treatment compositions in which microdried bacteria and a chemical substance toxic to the bacteria are combined. The compositions are fluid suspensions of the toxic chemical substances and the bacteria in a non-deleterious liquid carrier. The suspension may be formed into a liquid colloid using a gelling agent.

The invention further relates to methods for prolonging the viability of microorganisms when combined with a chemical substance which is normally toxic to the microorganism.

Specifically, microdried rhizobia, when suspended in a mineral oil-gel matrix, are protected and their viability prolonged when in combination with a fungicide and/or a molybdenum compound normally toxic to rhizobia.

DETAILED DESCRIPTION OF THE INVENTION

This invention relates to a method for preserving and stabilizing legume root nodule bacteria and other microorganisms in combination with chemical substances which are normally toxic to the microorganisms. In accordance with the present invention a liquid seed treatment composition is provided in which bacteria are combined with chemical substances normally having a toxic effect on bacteria. The compositions of the invention are prepared by combining the dried bacteria in a non-bactericidal, non-phytotoxic liquid carrier with the remaining ingredients of a particular formulation to form a liquid suspension.

More particularly, the compositions of the invention comprise microdried bacteria in a non-bactericidal, non-phytotoxic liquid carrier in a fluid suspension with the remaining ingredients, including the toxic chemical substances. The ingredients must be thoroughly dispersed throughout the suspension. A gelling agent may be added to create an oil-gel matrix which maintains the dispersion of the ingredients for a period of time.

Several procedures are available for drying bacteria. One highly satisfactory drying method for use in the practice of the present invention is the oil drying method described in U.S. Pat. No. 3,034,968 to Johnston. When used herein, the term "oil-dried bacteria" refers to bacteria prepared according to the method of this patent.

In accordance with the method described in that patent, bacteria are dried by suspending bacteria in a non-deleterious liquid and evaporating the moisture from the bacteria while so suspended. Suitable suspending liquids include liquid oils of mineral, vegetable or animal origin. Evaporation may be achieved by intimately contacting the suspension with a non-deleterious gas, such as air or nitrogen. The suspending liquid may be removed from the dried bacteria by various methods, including centrifugation or decantation.

The bacteria prepared by the oil-drying method provide a compact cell paste which is miscible in mineral oil. On the other hand, freeze-drying microorganisms, such as bacteria, destroys many of the organisms and, therefore, a large volume of cell paste is required for an adequate viable count. This fact plus the lack of miscibility of these aqueous phase freeze-dried pastes in mineral oil makes freeze-dried bacteria impractical for use in the compositions of the invention. Oil-dried bacteria are the microdried bacteria of choice for use in the compositions and methods of the invention.

According to the practice of the invention, the microdried bacteria are added to a liquid carrier which is not toxic or otherwise detrimental to the viability and effectiveness of the bacteria. The carrier selected also should not affect the germination or seedling emergence of the seed to which it is to be applied. Mineral oil is one carrier which has the above qualities and has proven highly effective in the practice of the invention. Various vegetable oils may also be used effectively in the compositions of the invention.

The compositions of the invention must be flowable to sustain and prolong bacterial viability. Thus, the amount of liquid carrier employed must be sufficient to maintain the composition in a fluid state after addition of all ingredients of a desired formulation. Generally, this requires at least fifty or more weight percent oil in the composition. However, the minimum amount of oil required in any particular formulation made according to the invention will depend on the nature of the ingredients and can readily be determined by one skilled in the art.

Virtually any type of chemical substance which has an adverse effect on bacteria is potentially usable in the invention. Contemplated within the scope of chemical substances to which the instant invention may be applied are agricultural chemicals having utility as fertilizers, fungicides, nematocides, insecticides, herbicides and growth regulants. Specifically, fungicides, such as Thiram (tetramethylthiuramdisulfide), have been used successfully in the practice of the invention. Molybdenum-containing compounds, which are toxic to bacteria, have also been effectively combined with bacteria in accordance with the invention. Specifically, sodium molybdate has been used in a formulation in accordance with the invention.

For maximum effectiveness, the ingredients of the compositions of the invention, particularly the bacteria, must remain thoroughly dispersed throughout the suspension. In order to maintain a thorough dispersion of the ingredients in the suspension, a gelling agent may be added to the composition to create an oil-gel matrix. This matrix allows suspension of the ingredients for extended periods of time. In addition, the matrix aids in minimizing contact between the bacteria and toxic chemical substances providing further protection for the bacteria. The functional life of the compositions is thereby extended and the viability of the bacteria is further prolonged.

One method for preparing an oil-gel matrix according to the invention is to suspend the bacteria in an oil carrier and then pour this suspension into a liquid, inert, clay gel matrix to which the toxic ingredients of the formulation have previously been added. By this means the components of the formulation are randomly distributed in the lattices of the gel.

Bacteria of the genus Rhizobium are effectively preserved and protected from toxic chemicals in accordance with the method of the invention. Specifically oil-dried *Rhizobium japonicum* has exhibited more stable and prolonged viability in the presence of a fungicide and a micronutrient when suspended in an oil-gel matrix.

In general, bacteria in the combination compositions of the invention have a prolonged period of viability relative to bacteria in non-fluid combination seed-treating compositions. Formation of the combination seed treatment compositions of the instant invention thus provides a method for prolonging bacterial viability in the presence of chemical substances normally toxic to bacteria.

The period of viability of a particular composition made according to the invention will of course be dependent on a number of factors known in the art to affect viability of bacteria as well as those taught in the present invention. Such factors include temperature, the nature and relative concentrations of the carrier, gellant, toxic chemical substance and bacteria. In general decreasing oil content, decreasing relative concentrations of bacteria to toxic substance or increasing temperature will reduce the period of viability of the compositions.

Since the compositions of the invention are liquid, they provide a more uniform coverage of the seed surface than the conventional dry seed treating compositions. This uniform seed coverage permits use of reduced amounts of active ingredients, such as fungicides, when applied in the compositions of the invention.

The following examples are illustrative of the invention:

EXAMPLE 1

The effects of reducing mineral oil content on oil-dried *Rhizobium japonicum* were studied in formulations containing the following ingredients: 12.6 g of a 90:10 quaternium — 18 hectorite clay gellant preblended in mineral oil, 17.2 g Thiram, 12.34 g Sodium Molybdate, 0.8 g charcoal and 0.038 g Rhizobia. The oil content was reduced by 10% increments from 105 g to 42 g. Using 105 g as the 100% concentration formulation the products below 60% oil concentration are not flowable. The contents of the samples were as follows:

|  | Formulation (Oil Concentration - %) | | | | | | |
|---|---|---|---|---|---|---|---|
|  | 100 | 90 | 80 | 70 | 60 | 50 | 40 |
| Wgt. of mineral oil (g) | 105 | 94.5 | 84.0 | 73.5 | 63.0 | 52.5 | 42.0 |
| Total weight/ bushel | 147.98 | 137.48 | 126.98 | 116.48 | 105.98 | 95.48 | 85.78 |
| Percent oil by wgt. | 71 | 68.8 | 66.2 | 63.1 | 59.5 | 55 | 48.9 |
| Plastic Viscosity* | 56 | 49 | 133 | 106 | 142 | — | — |

*Determined by Baroid Variable Speed Rheometer

The formulations were incubated at 90° F. and tested at five day intervals for viable rhizobia and ability to form nodules on soybean roots. For comparative purposes a conventional dry formulation containing rhizobia, Thiram and sodium molybdate was also tested. The results are set forth in Tables I and II respectively.

TABLE I

The effect of mineral oil concentration on longevity of *R. japonicum* (viable rhizobia/gram)

| Time (days) | Oil Concentration (%) | | | | | |
|---|---|---|---|---|---|---|
|  | 100 | 90 | 80 | 70 | 60 | Dry |
| 0 | $1.7 \times 10^7$ | $2.4 \times 10^7$ | $1.5 \times 10^7$ | $1.4 \times 10^7$ | $1.4 \times 10^7$ | $4.6 \times 10^7$ |

TABLE I-continued

The effect of mineral oil concentration on longevity of R. japonicum (viable rhizobia/gram)

| Time (days) | Oil Concentration (%) | | | | | |
|---|---|---|---|---|---|---|
| | 100 | 90 | 80 | 70 | 60 | Dry |
| 5 | $6.0 \times 10^6$ | $5.5 \times 10^6$ | $5.9 \times 10^6$ | $4.5 \times 10^6$ | $2.8 \times 10^6$ | $5.9 \times 10^5$ |
| 10 | $4.1 \times 10^6$ | $4.5 \times 10^6$ | $5.2 \times 10^6$ | $6.2 \times 10^6$ | $6.5 \times 10^6$ | $2.3 \times 10^4$ |
| 15 | $5.6 \times 10^5$ | $3.1 \times 10^5$ | $1.8 \times 10^5$ | $1.1 \times 10^5$ | $9.0 \times 10^5$ | $<10^4$ |
| 20 | $<10^4$ | $<10^4$ | $<10^4$ | $<10^4$ | $<10^4$ | $<10^4$ |

TABLE II

The effect of mineral oil concentration on nodulation of soybeans by rhizobia

| Time (days) | Dilution[1] | Oil Concentration | | | | | |
|---|---|---|---|---|---|---|---|
| | | 100 | 90 | 80 | 70 | 60 | Dry |
| 0 | $10^{-4}$ | 2.25[2] | 3.0 | 3.25 | 1.0 | 2.75 | 1.3 |
| 5 | $10^{-4}$ | 1.29 | 1.38 | 1.4 | 1.8 | 1.57 | 1.3 |
| 10 | $10^{-3}$ | 2.0 | 2.67 | 2.57 | 2.5 | 2.0 | 1.3 |
| 15 | $10^{-3}$ | 2.4 | 2.2 | 2.7 | 1.8 | 2.0 | 1.0 |
| 20 | $10^{-3}$ | 3.0 | 2.3 | 2.5 | 2.7 | 1.8 | 1.0 |

[1]Dilution of formulation used to inoculate seeds.
[2]Rating system; 5.0 = excellent nodulation, 1.0 = no nodulation.

The data generally indicates that the longevity of rhizobia is not significantly affected by reducing the mineral oil concentration from the 100 to 60 percent in the formulations. However, the rhizobia in the dry formulation die more rapidly than those in the liquid products. Similarly, the nodulation ratings between the liquid formulations were not significantly different, whereas the dry formulation caused less nodule formulation than any liquid product tested.

EXAMPLE 2

The effects of reducing mineral oil content on oil-dried Rhizobium japonicum were studied in formulations containing the following ingredients: 12.6 g of a 90:10 quaternium — 18 hectorite clay gellant preblended in mineral oil, 28.6 g Thiram, 12.34 g Sodium Molybdate, 0.8 g charcoal and 0.041 g rhizobia. The oil content was reduced from 105 g as in Example 1. Below the formulation having 70% oil concentration, the product was not flowable.

The formulations were incubated at 90° F. and tested at 5 day intervals for viable rhizobia and nodulation. The results are set forth in Tables III and IV respectively.

TABLE III

The effect of mineral oil concentration on longevity of R. Japonicum (viable rhizobia/gram)

| Time (days) | Oil Concentration (%) | | | | |
|---|---|---|---|---|---|
| | 100 | 90 | 80 | 70 | Dry |
| 0 | $1.7 \times 10^7$ | $2.2 \times 10^7$ | $1.3 \times 10^7$ | $1.2 \times 10^7$ | $4.6 \times 10^7$ |
| 5 | $1.6 \times 10^6$ | $1.1 \times 10^6$ | $2.0 \times 10^6$ | $8.0 \times 10^5$ | $5.9 \times 10^5$ |
| 10 | $1.3 \times 10^5$ | $4.5 \times 10^5$ | $2.2 \times 10^5$ | $2.6 \times 10^5$ | $2.3 \times 10^4$ |
| 15 | $3.0 \times 10^4$ | $4.0 \times 10^4$ | $3.0 \times 10^4$ | $3.1 \times 10^4$ | $<10^4$ |
| 20 | $<10^4$ | $<10^4$ | $<10^4$ | $<10^4$ | $<10^4$ |

TABLE IV

The effect of mineral oil concentration on nodulation of soybeans by rhizobia

| Time (days) | Dilution[1] | Oil Concentration | | | | |
|---|---|---|---|---|---|---|
| | | 100 | 90 | 80 | 70 | Dry |
| 0 | $10^{-4}$ | 2.5[2] | 2.0 | 3.0 | 1.5 | 1.3 |
| 5 | $10^{-4}$ | 1.3 | 1.8 | 1.0 | 1.5 | 1.3 |
| 10 | $10^{-3}$ | 1.75 | 2.2 | 1.25 | 2.0 | 1.3 |
| 15 | $10^{-3}$ | 2.0 | 2.0 | 2.2 | 1.3 | 1.0 |
| 20 | $10^{-3}$ | 1.25 | 1.5 | 1.5 | 1.75 | 1.0 |

[1]Dilution of formulation used to inoculate seeds.
[2]Rating system; 5.0 = excellent nodulation; 1.0 = no nodulation.

The liquid formulations as in Example 1 showed no significant differences in longevity of rhizobia or nodulation among themselves but all liquid formulations were superior to the dry formulation in both rhizobial longevity and nodulation.

EXAMPLE 3

The effects of reducing mineral oil content on oil-dried Rhizobium japonicum were studied in formulations containing the following ingredients: 12.50 g of 90:10 quaternium — 18 hectorite clay gellant preblended in mineral oil, 1.10 g silica, 0.80 g charcoal, 12.34 g Sodium Molybdate and 0.17 g Rhizobia. The oil content was reduced and below 70.5 wgt-% the product was not flowable. The formulations tested had the following oil content:

| | | | |
|---|---|---|---|
| Wgt. of Mineral Oil (g) | 106.25 | 85.00 | 63.80 |
| Percent oil by weight | 79.9 | 76.0 | 70.5 |

For comparison purposes, a conventional powder formulation containing 8 wgt.% oil was tested. The samples were incubated at 90° F. and tested at 5 day intervals for viable rhizobia. The results are set forth in Table V.

TABLE V

Effect of oil concentration on longevity or R. japonicum (viable rhizobia/gram)

| Time (days) | Oil Concentration (wgt.-% of Formulation) | | | |
|---|---|---|---|---|
| | 78.9 | 76.0 | 70.5 | Dry |
| 0 | $1.4 \times 10^8$ | $9.9 \times 10^7$ | $1.2 \times 10^8$ | $7.8 \times 10^6$ |
| 5 | $4.5 \times 10^7$ | $2.8 \times 10^7$ | $3.8 \times 10^7$ | $0.7 \times 10^6$ |
| 10 | $3.8 \times 10^7$ | $4.0 \times 10^7$ | $4.2 \times 10^7$ | $1.0 \times 10^6$ |
| 15 | $5.5 \times 10^6$ | $6.6 \times 10^6$ | $7.1 \times 10^6$ | 0 |
| 20 | $1.6 \times 10^6$ | $1.5 \times 10^6$ | $2.2 \times 10^6$ | 0 |
| 30 | $1.7 \times 10^6$ | $2.0 \times 10^6$ | $2.2 \times 10^6$ | 0 |

The data indicates that reducing oil concentration to 70.5 wgt-% does not significantly affect rhizobial activity. However, the survival rate was much lower in the dry formulation than in any of the liquid formulations.

What is claimed is:

1. A liquid seed treating composition which comprises a fluid suspension of microdried bacteria and a chemical substance toxic to the bacterium in a non-phytotoxic, non-bactericidal oil carrier.

2. The composition of claim 1 wherein the oil carrier is mineral oil.

3. The composition of claim 1 which further comprises a gelling agent which with the carrier forms an oil-gel matrix.

4. The composition of claim 1 wherein the microdried bacterium is oil dried.

5. The composition of claim 1 wherein the bacterium is selected from the genus Rhizobium.

6. The composition of claim 1 wherein the chemical substance toxic to the bacterium is a fungicide.

7. The composition of claim 1 wherein the chemical substance toxic to the bacterium is tetramethylthiuramdisulfide.

8. The composition of claim 1 wherein the chemical substance toxic to the bacterium is a micronutrient.

9. The composition of claim 1 wherein the chemical substance toxic to the bacterium is a molybdenum containing compound.

10. A method of prolonging the viability of a microorganism when combined with a chemical substance which is normally toxic to the microorganism which comprises flowably suspending a microdried bacterium and a chemical substance normally toxic to the bacterium in a non-phytotoxic, non-bactericidal oil carrier.

11. The method according to claim 10 in which the oil carrier is mineral oil.

12. The method according to claim 10 which further comprises forming an oil-gel matrix by adding a gelling agent to the oil.

13. The method according to claim 10 in which the bacterium is a member of the genus Rhizobium.

14. The method of claim 10 in which the chemical substance is tetramethylthiuramdisulfide.

15. The method of claim 10 in which the chemical substance is a molybdenum compound.

* * * * *

UNITED STATES PATENT OFFICE
CERTIFICATE OF CORRECTION

PATENT NO. : 4,161,397
DATED : July 17, 1979
INVENTOR(S) : Eugene M. Bellet and Madan M. Joshi It is certified that error appears in the above-identified patent and that said Letters Patent are hereby corrected as shown below:

Column 5, the 7th line of Table 1, "15  $5.6 \times 10^5$  $3.1 \times 10^5$  $1.8 \times 10^5$  $1.1 \times 10^5$  $9.0 \times 10^5$  $< 10^4$" should read --15  $5.6 \times 10^5$  $3.1 \times 10^5$  $1.8 \times 10^5$  $1.1 \times 10^5$  $9.0 \times 10^4$  $< 10^4$--.

Column 5, the 5th line of Table IV, "0  $10^{-4}$  $2,5^2$  2.0  3.0  1.5  1.3" should read --0  $10^{-4}$  $2.5^2$  2.0  3.0  1.5  1.3--.

Signed and Sealed this

Thirteenth Day of November 1979

[SEAL]

Attest:

RUTH C. MASON
*Attesting Officer*

LUTRELLE F. PARKER
*Acting Commissioner of Patents and Trademarks*